United States Patent [19]
Van Syckle et al.

[11] Patent Number: 5,009,666
[45] Date of Patent: Apr. 23, 1991

[54] PLUG AND METHOD OF USE

[76] Inventors: Peter B. Van Syckle; Glen A. Kashuba, both of Pfizer Inc., 235 E. 42nd St., New York, N.Y. 10017-5755

[21] Appl. No.: 462,302

[22] Filed: Dec. 21, 1989

Related U.S. Application Data

[63] Continuation of Ser. No. 252,231, Sep. 30, 1988, abandoned.

[51] Int. Cl.$^5$ ............ A61F 2/32; A61F 2/28; A61F 5/04
[52] U.S. Cl. .................. 623/23; 623/16; 623/18; 606/60
[58] Field of Search ............. 623/11–13, 623/16, 17, 18, 19, 20, 21, 22, 23; 606/60, 61, 62, 67, 69, 71, 72, 77

[56] References Cited

U.S. PATENT DOCUMENTS

| | | | |
|---|---|---|---|
| Re. 32,488 | 9/1987 | Bustelo et al. | 623/23 |
| 3,805,300 | 4/1974 | Tascon-Alonso et al. | 623/15 |
| 3,890,107 | 6/1975 | White et al. | 29/183 |
| 4,217,664 | 8/1980 | Faso | 623/11 |
| 4,365,358 | 12/1982 | Judet et al. | 623/22 |
| 4,563,778 | 1/1986 | Roche et al. | 623/11 |
| 4,596,248 | 6/1986 | Lieberman | 128/207.16 |
| 4,623,348 | 11/1986 | Felt | 623/11 |
| 4,792,339 | 12/1988 | Tepi | 623/23 |
| 4,842,606 | 6/1989 | Kranz et al. | 623/23 |

FOREIGN PATENT DOCUMENTS

| | | | |
|---|---|---|---|
| 0024442 | 3/1981 | European Pat. Off. | 623/22 |
| 0244720 | 11/1987 | European Pat. Off. | 623/18 |

*Primary Examiner*—David J. Isabella

[57] ABSTRACT

A plug for use with a fenestrated prosthesis is provided. The plug and prosthesis combination are to be used when the fenestrated prosthesis is used with bone cement.

A method of using the fenestrated prosthesis and plug combination with bone cement is also given.

6 Claims, 1 Drawing Sheet

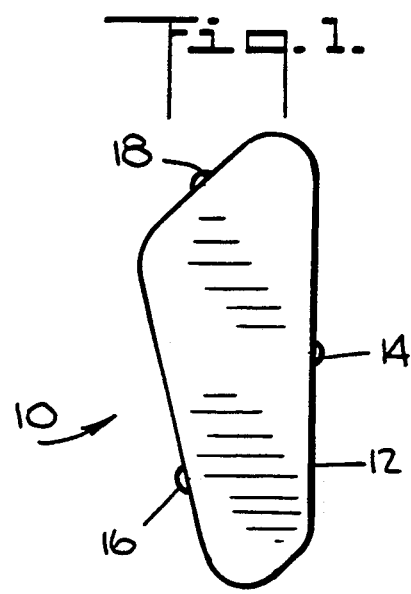
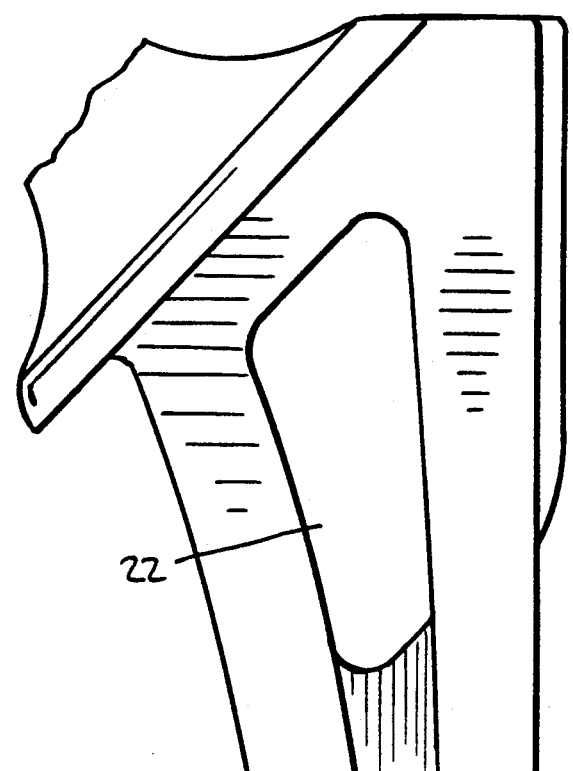
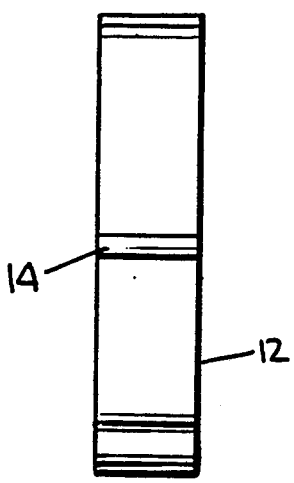
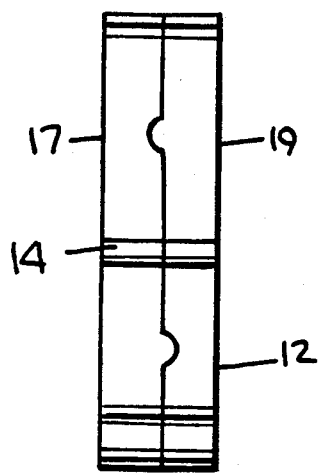

PLUG AND METHOD OF USE

This application is a continuation of application Ser. No. 252,231, filed Sept. 30, 1988, now abandoned.

BACKGROUND OF THE INVENTION

This invention relates generally to orthopedics and more particularly to prostheses which are to be implanted with bone cement.

In orthopedics, it is desirable to have a relatively limited number of shelf items which can be used for a variety of purposes. For example, it is desirable to have a type of prosthesis which can be used either with or without bone cement, depending upon the needs of the individual patient.

In the past, it has been known to use designs for stems of hip prostheses which are of the type called "Moore" stem designs. In these designs, bone in the form of a plug is placed into a hole in the prosthesis for the purpose of promoting bone ingrowth of the patient into the prosthesis. The patient's bone then will fuse with the bone plug.

For cemented prostheses, generally in the prior art, a prosthesis having a design in which no holes are present is used. This is so because if there is a need to remove the cemented prosthesis from the patient at a later date, the bone cement should not be lodged within the prosthesis itself.

An object of this invention is a system which can be used both with or without bone cement and which, therefore, will provide the orthopedic surgeon a certain level of choice so that the number of stock items can be reduced.

SUMMARY OF THE INVENTION

According to the invention, a plug is provided for use with a fenestrated prosthesis (i.e., a prosthesis having at least one opening or hole therein), the plug being of a relatively flexible and biocompatible material and of a shape substantially similar to the shape of the fenestration and of a size slightly larger than the size of the fenestration.

Also according to the invention, the above-described plug and the above-described fenestrated prosthesis provide a system which is suitable for use in patients requiring a prosthesis cemented within a bone canal.

Further, according to the invention, a method of using a fenestrated prosthesis and a fenestration plug of the invention in patients requiring a cemented prosthesis is provided, the method comprising inserting a fenestration plug into the fenestrated prosthesis prior to implanting the prosthesis into a bone canal of a patient with bone cement.

BRIEF DESCRIPTION OF THE DRAWINGS

FIG. 1 is a plan view of an embodiment of a fenestration plug of the invention.

FIG. 2 is an end view of the embodiment of the plug shown in FIG. 1.

FIG. 3 is an end view of an embodiment of a plug formed from two pieces interlocking in a tongue and groove arrangement.

FIG. 4 is a plan view of a portion of a fenestrated hip prosthesis suitable for use with the plug of FIG. 1 in a patient in which that prosthesis is to be implanted with bone cement. The head and distal end of the prosthesis are not shown.

DETAILED DESCRIPTION OF THE PREFERRED EMBODIMENTS

In FIG. 1 and FIG. 2, a preferred embodiment of a fenestration plug (referred to generally as 10) is shown. The outer periphery 12 of plug 10 has ribs 14, 16, and 18. In FIG. 1, although three ribs are shown, the number can be chosen as desired. Alternatively, it may be desirable to have no ribs. The ribs in FIG. 1 are an integral part of plug 10, and when plug 10 is made of a flexible material as described below, the ribs enable the plug to be press-fit into a fenestration, as described below.

Although in FIG. 1 and FIG. 2, plug 10 is a single piece of material, if desired plug 10 can be made from more than one piece. For example, if desired, plug 10 can be made of two interlocking pieces 17, 19, which fit together so as to form one plug, as shown for example in FIG. 3.

In FIG. 4, a portion of a prosthesis 20 suitable for use in an intramedullary canal of a hip is shown. Prosthesis 20 has a fenestration 22 which has substantially the same shape as fenestration plug 10 shown in FIG. 1. Plug 10, as described above, has ribs 14, 16, 18, which provide a plug having a size slightly larger than fenestration 22. Thus, plug 10 can be press-fit into fenestration 22, thus providing a system 23 of plug 10 located within prosthesis 20 which is suitable for use when prosthesis 20 is to be implanted within a patient with bone cement. Plug 10 prevents bone cement from filling fenestration 22. Thus, after prosthesis 20 has been implanted into a patient's intramedullary canal with bone cement, if necessary the prosthesis 20 can be later removed quite easily because the bone cement has not filled fenestration 22.

Prosthesis 20 having fenestration 22 can also be used, if desired, without fenestration plug 10. In that case, no bone cement would be used. If desired, a bone plug can be placed into fenestration 22, as has been known in the prior art, so as to promote bone ingrowth into the fenestration when it is used in a press-fit application, without bone cement. Thus, the prosthesis 20 having fenestration 22 can be used for cement applications or for cementless application. Thus, it is seen that the fenestration plug 10 provides an option of modularity to this fenestrated prosthesis 20.

The materials for forming fenestration plug 10 will be selected from the group of materials which are relatively flexible and biocompatible and do not react with bone cement. Examples of suitable materials include but are not limited to polyurethane and silicone (for example, grades MDX4-4515 and MDX4-4516). These materials are flexible, gummy, and biocompatible materials, and they are especially preferred. However, other materials having similar characteristics can also be used for producing the fenestration plug 10, for example polyethylene.

The shape of the fenestration plug 10 can be chosen as desired, provided that it fits within the fenestration of the prosthesis and securely fills the fenestration. For certain purposes, it may be desirable to use a fenestration plug in the shape of a circle or another shape.

The shape of fenestration plug 10 shown in FIG. 1 was chosen so that it fills fenestration 22 of prosthesis 20 shown in FIG. 2. The shape of fenestration 22 shown in FIG. 2 was selected so that compressive forces would push down on prosthesis 20, thus resulting in a prosthesis 20 having relatively high strength.

In using the system 23 of the prosthesis 20 with fenestration 22 and fenestration plug 10, one inserts plug 10 within fenestration 22 prior to implanting the prosthesis 20. The system 23 of prosthesis 20 and plug 10 is inserted into the bone canal containing cement.

We claim:

1. A biocompatible insert for use in filling a fenestration that extends through an implant member wherein the fenestration is of a predetermined shape and depth, said insert comprising at least two discs made of a relatively flexible material, each of said discs having a predetermined thickness and an outer perimeter defining a shape substantially identical to the predetermined shape of said fenestration, each of said discs having a plurality of ribs integrally formed about said outer perimeter thereof and interlocking means for interlocking said discs together to form said insert so that when said insert is press-fitted within said fenestration, the combined thickness of the discs is substantially equal to said predetermined depth of the fenestration in said implant, thereby completely filling the fenestration.

2. An insert according to claim 1, wherein said discs having a shape which is substantially rectangular with rounded corners.

3. An insert according to claim 1, wherein said relatively flexible material is biocompatible and selected from the group consisting of polyurethane and silicone.

4. An insert according to claim 1, wherein said insert has a generally trapezoidal shape conforming to a substantially identical fenestration shape in the implant.

5. An insert according to claim 1, wherein said predetermined shape is substantially circular.

6. A method of implanting with bone cement an implant having a fenestration of predetermined shape and depth extending therethrough, the method comprising:

providing at least two discs made of a relatively flexible material, each of said discs having a predetermined thickness and an outer perimeter defining a shape of said fenestration, each of said discs having a plurality of ribs integrally formed about said outer perimeter thereof;

joining the discs to form a biocompatible insert having a combined thickness being substantially equal to said predetermined depth of the fenestration in said implant;

press-fitting said biocompatible insert within said fenestration to completely fill the fenestration; and implanting said prosthesis.

* * * * *